United States Patent [19]

Morgan, Jr. et al.

[11] Patent Number: 5,252,713
[45] Date of Patent: Oct. 12, 1993

[54] POLYMERIC CARRIERS FOR NON-COVALENT DRUG CONJUGATION

[75] Inventors: Alton C. Morgan, Jr., Edmonds; David C. Anderson, Seattle, both of Wash.

[73] Assignee: NeoRx Corporation, Seattle, Wash.

[21] Appl. No.: 248,456

[22] Filed: Sep. 23, 1988

[51] Int. Cl.[5] ............... A61K 37/02; A61K 39/44; C07K 3/08

[52] U.S. Cl. ............... 530/391.7; 424/85.91; 435/188; 530/350; 530/351; 530/362; 530/363; 530/391.9; 530/392; 530/399; 530/402

[58] Field of Search ............... 530/350, 387, 402, 362, 530/363, 391.7, 391.9, 392, 387.3, 351, 399; 424/85.91; 435/188; 514/2

[56] References Cited

U.S. PATENT DOCUMENTS

| | | | |
|---|---|---|---|
| 4,046,722 | 9/1977 | Rowland | 260/6 |
| 4,414,148 | 11/1983 | Jansen et al. | 260/112 |
| 4,500,707 | 2/1985 | Caruthers et al. | 536/27 |
| 4,534,971 | 8/1985 | Fisher | 530/350 |
| 4,599,311 | 7/1986 | Kawasaki | 435/71 |
| 4,642,335 | 2/1987 | Miyashiro et al. | 530/409 |
| 4,659,839 | 4/1987 | Nicolotti et al. | 548/546 |
| 4,668,777 | 5/1987 | Caruthers et al. | 536/27 |
| 4,671,958 | 6/1987 | Rodwell et al. | 424/85 |
| 4,680,338 | 7/1987 | Sundoro | 525/54.1 |
| 4,684,723 | 8/1987 | Dove et al. | 530/351 |
| 4,699,784 | 10/1987 | Shih et al. | 424/85 |
| 4,704,362 | 11/1987 | Itakura et al. | 435/253 |
| 5,106,951 | 4/1992 | Morgan, Jr. et al. | 530/402 |

FOREIGN PATENT DOCUMENTS

WO86/00528 1/1986 PCT Int'l Appl. .
2119804A 11/1983 United Kingdom .

OTHER PUBLICATIONS

J. Immunology, vol. 139, No. 7, issued Oct. 1, 1987, Glennie et al, "Preparation and Performance of Bispecific F(ab'γ)2 Antibody . . . ", pp. 2367–2375.
Ghose et al. Methods Enzymol. vol. 45 pp. 280–333 (1983).
Fisher et al., Biochemistry vol. 21(24) pp. 6172–6180 (1982).
Lawn et al., Nucleic Acids Research 9:6103–14, No. 22, 1981.
Blair et al., J. Immunol. Meth. 59:129–43, 1983.
Crestfield et al., J. Biol. Chem. 238:622–627, 1963.
Merrifield et al., Biochemistry 21:5020–31, 1982.
Houghten, PNAS 82:5131–35, 1985.
Tam et al., J. Am. Chem. Soc. 105:6442–55, 1983.
Heinrikson et al., Anal. Biochem. 136:65–74, 1984.
Meltzer et al., Anal. Biochem. 160:356–61, 1987.
Storms et al., J. Bacteriology 140:73–82, 1979.
Blanc et al., Molec. gen. Genet. 176:335–42, 1979.
Kessler, J. Immunology 117:1432–90, 1976.
Old and Primrose, Principals of Gene Manipulation, 2nd edition, University of California Press, 1981, pp. 32–35, 46–47, 51–53, 62–68, chapter 5, pp. 92, 104–117.
Stewart and Young, Solid Phase Peptide Synthesis, published by W. H. Freeman and Company, 1969.
Laemmli, Nature 227:680–85, 1970.
PIR Protein Sequence Database, Directory of Online Databases, vol. 11, No. 3, p. 402.
Protein Identification Resource (PIR), Information Industry Directory, 11th Edition, 1991, p. 870.
Pierce Chemical Company General Catalog, pp. E4–E14, E31–E33, and E39–E48.
Bos et al., Biochimica et Biophysica Acta 953:37–47, 1988.
Chignell, Handbook of Biochemistry and Molecular Biology, pp. 554–581.

Primary Examiner—Jeffrey E. Russel
Attorney, Agent, or Firm—Burns, Doane, Swecker & Mathis

[57] ABSTRACT

Polymeric carriers are polypeptides comprising at least one drug-binding domain that non-covalently binds a drug. A polymeric carrier may be attached to an antibody specific for desired target cells to form immunoconjugates that deliver a drug to the target cells in vivo. The carriers are derived from drug-binding proteins and produced through peptide synthesis or recombinant DNA technology.

18 Claims, No Drawings

POLYMERIC CARRIERS FOR NON-COVALENT DRUG CONJUGATION

DESCRIPTION

Technical Field

The present invention relates to compositions and methods for making polymeric carriers for non-covalent binding of drugs. The polymeric carriers are capable of binding one or multiple drug molecules. The polymeric carriers are then covalently attached to a targeting protein, such as an antibody molecule, thereby forming an antibody/polymeric carrier/drug conjugate for targeting to defined populations of cells, such as cancer cells.

BACKGROUND OF THE INVENTION

There has been considerable interest in developing methods of attaching various diagnostic and therapeutic agents to targeting proteins such as antibodies. Recent efforts include the conjugation of therapeutic agents, such as cytotoxic or antineoplastic drugs, to specific antibodies, such as monoclonal antibodies, to produce conjugates which can selectively target tumor cells while sparing normal tissues.

A large number of different classes of therapeutic agents have been considered, including beta-, gamma-, and alpha-emitting radioisotopes; plant and bacterial toxins; and a variety of antineoplastic drugs, including intercalating agents, antimetabolites, alkylating agents, and antibiotics. It is desirable to conjugate chemotherapeutic drugs to targeting molecules such as antibodies for the following reasons:

1. It has recently been shown that up to 1,000fold more drug can be delivered to tumor cells when conjugated to an antigen-specific monoclonal antibody than is possible by the addition of free drug.

2. Pleiotropic drug resistance may arise following treatment with one of a number of chemotherapeutic drugs, resulting in inducing resistance to drugs of several classes. The mechanism(s) of this resistance are not entirely known, but it is known that this resistance can be partially overcome by antibody targeting of drugs.

3. Even though current chemotherapeutic drugs are active against only some of the major tumor types, the response rate in drug-insensitive tumor types may be increased by antibody-mediated delivery.

4. Many dose-limiting toxicities which are now seen with chemotherapeutic drugs can be reduced by conjugation to an antibody. A decrease in toxicity with concomitantly at least equal efficacy would provide a superior product with a higher therapeutic index.

To create a conjugate with a therapeutic agent and an antibody, the therapeutic agent may be directly linked to the antibody through nucleophilic substitution of certain groups on the antibody (e.g., amino, carboxyl, or sulfhydryl) or the drug may be conjugated to the antibody via a hetero- or homobifunctional cross-linker.

The linking group generally is heterobifunctional, having two different functionalities, one of which reacts with the drug and the other with the antibody. Linking groups may be small or quite long. For example, a relatively small linking group is carbonyl diimidazole. Large proteins or polymers, ("carriers") have also been used as linking groups and offer the advantage of being able to bind many drug molecules to a single antibody molecule. Examples of large proteins or polymers are poly-L-lysine, polyglutamate, dextran, and albumin, all of which have molecular weights in excess of 5000 daltons. These carriers generally are derivatized with small linking groups to bind drugs. See, for example, U.S. Pat. Nos. 4,699,784 and 4,046,722.

Drug conjugation to a protein or an antibody targeting molecule has generally been through covalent binding of the drug to the antibody directly or by covalently binding the drug molecule to the linking group. (Blair et al., *J. Immunol. Meth.* 59:129-44, 1983.) Even when the drug is linked to a carrier molecule such as albumin or dextran, the drug undergoes a modification to allow for the covalent conjugation of the drug. The drug modification often results in the loss of some of the activity of the drug molecule due to chemical modifications of some of the functional groups within the drug molecule.

In the case of some drug molecules, exposure to derivatization conditions may completely inactivate the drug. For other drug molecules, the derivatization may not be completely specific for groups intended for linkage but may also modify groups important for drug activity.

Accordingly, there exists a need in the field of drug conjugation to be able to attach multiple drug molecules to the targeting antibody without covalent modification of the drug and loss of drug activity.

SUMMARY OF THE INVENTION

The present invention provides polymeric carriers comprising at least one drug-binding domain derived from a protein, wherein each drug-binding domain can non-covalently bind a drug. The polymeric carrier preferably comprises multiple drug-binding domains, wherein the domains may be the same or different and therefore may bind the same or different drugs.

The polymeric carrier may be attached to a targeting protein, such as an antibody, that binds to a desired target site in vivo. The present invention thus provides targeting protein/polymeric carrier/drug conjugates comprising a targeting protein covalently bound to a polymeric carrier, wherein said polymeric carrier comprises one or more drug-binding domains having a drug non-covalently bound thereto, wherein each of said domains is derived from a drug-binding protein. The targeting protein may be covalently bonded to the polymeric carrier directly or through a linker molecule. Pharmaceutical preparations comprising such a conjugate in an aqueous solution (for in vivo administration for therapeutic purposes) also are disclosed.

The present invention also provides methods for producing polymeric carriers. The carriers are derived from relatively large molecular weight proteins, and may be produced by such methods as peptide synthesis or recombinant DNA technology.

A method for preserving the therapeutic activity of a drug also is disclosed, said method comprising non-covalently binding the drug to a polymeric carrier. The drug activity is thus preserved during subsequent chemical reactions, such as the reactions used to attach the polymeric carrier to a targeting protein to form a conjugate. Drug activity also is preserved in vivo after administration of the conjugate to a human or mammalian host.

DETAILED DESCRIPTION OF THE INVENTION

Prior to describing the invention in detail, it is helpful to set forth certain definitions.

Polymeric Carrier: By the term "polymeric carrier" is meant a polymer, such as a polypeptide, comprising one or more drug-binding domains wherein the domains are capable of binding a drug through non-covalent bonds. The polymeric carriers of the present invention are not naturally occurring, but are derived from naturally occurring proteins. A polymeric carrier may comprise one or multiple drug-binding domains fabricated through such methods as peptide synthesis or recombinant DNA technology. The domains may then be polymerized to produce a multi-domain polymeric carrier. A polymeric carrier of the present invention is able to non-covalently bind at least one drug through one or more non-covalent interactions or reversible interactions.

Covalent Bond: A "covalent bond" is defined as the formation of a sigma bond between two organic molecules.

Non-covalent Bond: A "non-covalent bond" is meant to include all interactions other than a covalent bond. Non-covalent bonds include ionic interactions, hydrogen bonding, pi-pi bonding, hydrophobic interactions, and van der Waals interactions.

The present invention addresses the problem of loss of drug activity due to attachment of drugs to various carriers through covalent bonds. Briefly stated, the present invention relates to a polymeric carrier containing one or multiple drug-binding domains (wherein each drug-binding domain non-covalently binds a drug), conjugates comprising a polymeric carrier bound to a targeting protein, and conjugates comprising one or more drug molecules non-covalently bound to a polymeric carrier which in turn is bound to a targeting protein. The targeting protein is a protein that binds to a desired target site in vivo, thereby delivering the conjugate to the target site. Targeting proteins include antibodies, and are described in more detail below. Also provided by the present invention are conjugates comprising a polymeric carrier as a drug active site protecting group. The polymeric carrier serves to protect the drug's active functional groups during the chemical reactions used to attach the polymeric carrier to a targeting protein. The polymeric carrier also protects the drug after in vivo administration of a drug(s)/polymeric carrier/ targeting protein conjugate and minimizes non-specific interactions of the drug moiety of the conjugate with cellular membranes.

Polymeric carriers are polymers such as polypeptides comprising one or a plurality of drug binding domains, which may be produced by such methods as peptide synthesis procedures or through cloning and expression of specific nucleotide sequences. The polymeric carrier preferably contains multiple drug-binding domains, wherein the drug-binding domain may be derived from a large molecular weight polymer such as a protein and then polymerized. The large protein can typically bind non-covalently only one or a few drug molecules. The polymeric carrier polypeptides may be synthesized as a single polypeptide chain or as disulfide-bonded peptide chains.

In another aspect, the present invention provides a method for producing polymeric carriers. These carriers are prepared by first identifying a protein, generally a large molecular weight protein, that is able to non-covalently bind a particular drug of interest. A drug-binding domain is then isolated from the protein, wherein the drug-binding domain is capable of binding a drug of interest through non-covalent means. Examples of large molecular weight proteins that can non-covalently bind to certain drug molecules include, but are not limited to, riboflavin-binding protein (RBP) to anthracyclines; albumin to certain lipophilic drugs such as anthracyclines, methotrexate, and cis-platinum; or one of the other proteins described below (e.g., in Table I).

Once the drug-binding domain in such proteins is identified and characterized (e.g., by determination of the amino acid sequence), the polymeric carriers may be produced through a variety of techniques. Such techniques include peptide synthesis to produce multiple copies of the domain, which may be joined to form a multi-domain polymeric carrier. Alternatively, single or multiple domain polymeric carriers may be produced through recombinant DNA technology.

Another aspect of the invention is a pharmaceutical composition which includes a conjugate comprising one or more drug molecules bound to a single- or multiple-domain polymeric carrier for prolonged serum half-life and increased efficacy. These slow-release pharmaceutical compositions may include a conjugate comprising a drug non-covalently bound to a polymeric carrier which in turn may be attached to a targeting protein. Alternatively, the conjugate may comprise a polymeric carrier bound to a targeting protein wherein the drug is to be added and non-covalently bound later, before use. The non-covalent binding of the drug in the conjugates of the present invention permits slow release of the drug from the polymeric carrier in vivo. "Slow release" means that the serum half life of the drug is increased compared to free drug. The patient's tissues are exposed to the drug for a longer period of time than when free (i.e., unconjugated) drug is administered, and therapeutic efficacy thus is enhanced.

It is preferable to isolate a drug-binding domain from a large molecular weight protein to form the conjugates of the invention because attaching a high molecular weight protein to a targeting protein may have an adverse effect on the desired biological activity (e.g., the "targeting" ability) of the targeting protein. For example, attaching the large protein to an antibody may impair the immunoreactivity and accessibility to tumors of the resulting immunoconjugate. This is especially true if more than one high molecular weight protein molecule is attached to a targeting protein molecule. For example, RBP is a 50-kilodalton glycoprotein that binds one mole of drug per mole of protein. Conjugation of multiple RBPs per antibody molecule would result in a conjugate with a molecular weight unacceptable for rapid extravasation and delivery to tumor sites. Accordingly, the use of just the drug-binding domain of RBP polymerized to give a polymeric carrier with multiple drug-binding domains would provide for non-covalent binding and delivery to target sites of multiple drug molecules per targeting protein, while reducing the size of the carrier protein to which the drug molecules are bound. The total molecular weight of the multi-domain polymeric carrier preferably is less than about 60,000 daltons.

Non-covalent binding of the drug preserves the activity of the drug, as discussed above. A polymeric carrier also serves to protect the active functional groups on the drug molecule by non-covalently binding to the drug molecule. The enveloping of the drug by the polymeric carrier serves to protect the functional groups of the drug molecule from any subsequent derivatization conditions (used to conjugate the carrier to the targeting protein) and to block nonspecific interactions between the drug functional groups and non-target cell surfaces during in vivo administration of the targeting protein conjugate.

The process of isolating a polymeric carrier from a drug-binding, large molecular weight protein begins with the identification of a large protein that can non-covalently bind the drug of interest. Examples of such protein/drug pairs are shown in Table I. The drugs in the Table (other than the steroids) are anti-cancer drugs.

TABLE I

| PROTEIN | DRUG |
| --- | --- |
| Riboflavin-Binding Protein | Doxorubicin, daunorubicin, and other anthracyclines |
| Alpha-1-acid glycoprotein | Doxorubicin, daunorubicin, other anthracyclines, vinblastine, mito-xantrone, ARA-C, 6-mercaptopurine, 6-mercaptoguanosine, and mitomycin C |
| Steroid-binding protein | Testosterone, estrogen derivatives |
| Estrogen receptor | Estrogens and derivatives thereof |
| Albumin | Doxorubicin, daunorubicin, other anthracyclines, cis-platinum, methotrexate |

Other drug-binding proteins may be identified by appropriate analytical procedures, including Western blotting of large proteins or protein fragments and subsequent incubation with a detectable form of drug. Alternative procedures include combining a drug and a protein in a solution, followed by size exclusion HPLC gel filtration, thin-layer chromatography (TLC), or other analytical procedures that can discriminate between free and protein-bound drug. Detection of drug binding can be accomplished by using radiolabeled, fluorescent, or colored drugs and appropriate detection methods. Equilibrium dialysis with labeled drug may be used. Alternative methods include monitoring the fluorescence change that occurs upon binding of certain drugs (e.g., anthracyclines or analogs thereof, which should be fluorescent). In one detection method, drug and protein are mixed, and an aliquot of this solution (not exceeding 5% of the column volume of an HPLC column, such as a Bio-sil TSK-250 7.5×30 cm column) is loaded onto the HPLC column. The flow rate is 1 ml/min. The drug bound to protein will elute first, in a separate peak, followed by free drug, eluting at a position characteristic of its molecular weight. If the drug is doxorubicin, both a 280-nm as well as a 495-nm adsorptive peak will correspond to the elution position of the protein if interaction occurs. The elution peaks for other drugs will indicate whether drug binding occurs.

Knowledge of the chemical structure of a particular drug (i.e., whether chemically reactive functional groups are present) allows one to predict whether covalent binding of the drug to a given protein can occur. Additional methods for determining whether drug binding is covalent or non-covalent include incubating the drug with the protein, followed by dialysis or subjecting the protein to denaturing conditions. Release of the drug from the drug-binding protein during these procedures indicates that the drug was non-covalently bound. Usually, a dissociation constant of about $10^{-15}M$ or less indicates covalent or extremely tight non-covalent binding.

During dialysis, non-covalently bound drug molecules are released over time from the protein and pass through a dialysis membrane, whereas covalently bound drug molecules are retained on the protein. An equilibrium constant of about $10^{-5}M$ indicates non-covalent binding. Alternatively, the protein may be subjected to denaturing conditions; e.g., by gel electrophoresis on a denaturing (SDS) gel or on a gel filtration column in the presence of a strong denaturant such as 6M guanidine. Covalently bound drug molecules remain bound to the denatured protein, whereas non-covalently bound drug molecules are released and migrate separately from the protein on the gel and are not retained with the protein on the column.

Once a protein that can non-covalently bind a particular drug of interest is identified, the drug-binding domain is identified and isolated from the protein by any suitable means. Protein domains are portions of proteins having a particular function or activity (in this case, non-covalent binding of drug molecules). The present invention provides a process for producing a polymeric carrier, comprising the steps of generating peptide fragments of a protein that is capable of non-covalently binding a drug and identifying a drug-binding peptide fragment, which is a peptide fragment containing a drug-binding domain capable of non-covalently binding the drug, for use as the polymeric carrier.

One method for identifying the drug-binding domain begins with digesting or partially digesting the protein with a proteolytic enzyme or specific chemicals to produce peptide fragments. Examples of useful proteolytic enzymes include lys-C-endoprotease, arg-C-endoprotease, V8 protease, endoprolidase, trypsin, and chymotrypsin. Examples of chemicals used for protein digestion include cyanogen bromide (cleaves at methionine residues), hydroxylamine (cleaves the Asn-Gly bond), dilute acetic acid (cleaves the Asp-Pro bond), and iodosobenzoic acid (cleaves at the tryptophane residue). In some cases, better results may be achieved by denaturing the protein (to unfold it), either before or after fragmentation.

The fragments may be separated by such procedures as high pressure liquid chromatography (HPLC) or gel electrophoresis. The smallest peptide fragment capable of drug binding is identified using a suitable drug-binding analysis procedure, such as one of those described above. One such procedure involves SDS-PAGE gel electrophoresis to separate protein fragments, followed by Western blotting on nitrocellulose, and incubation with a colored drug like adriamycin. The fragments that have bound the drug will appear red. Scans at 495 nm with a laser densitometer may then be used to analyze (quantify) the level of drug binding.

Preferably, the smallest peptide fragment capable of non-covalent drug binding is used. It may occasionally be advisable, however, to use a larger fragment, such as when the smallest fragment has only a low-affinity drug-binding domain.

The amino acid sequence of the peptide fragment containing the drug-binding domain is elucidated. The purified fragment containing the drug-binding region is denatured in 6M guanidine hydrochloride, reduced and carboxymethylated by the method of Crestfield et al., *J. Biol. Chem.* 238:622, 1963. As little as 20 to 50 picomoles of each peptide fragment can be analyzed by automated Edman degradation using a gas-phase or liquidpulsed protein sequencer (commercially available from Applied Biosystems, Inc.). If the peptide fragment is longer than 30 amino acids, it will most likely have to be fragmented as above and the amino acid sequence patched together from sequences of overlapping fragments.

Once the amino acid sequence of the desired peptide fragment has been determined, the polymeric carriers can be made by either one of two types of synthesis. The first type of synthesis comprises the preparation of each peptide chain with a peptide synthesizer (e.g., commercially available from Applied Biosystems). The second method utilizes recombinant DNA procedures.

Peptide amides can be made using 4-methylbenzhydrylamine-derivatized, cross-linked polystyrene-1% divinylbenzene resin and peptide acids made using PAM (phenylacetamidomethyl) resin (Stewart et al., "Solid Phase Peptide Synthesis," Pierce Chemical Company, Rockford, Ill., 1984). The synthesis can be accomplished either using a commercially available synthesizer, such as the Applied Biosystems 430A, or manually using the procedure of Merrifield et al., *Biochemistry* 21:5020-31, 1982; or Houghten, *PNAS* 82:5131-35, 1985. The side chain protecting groups are removed using the Tam-Merrifield low-high HF procedure (Tam et al., *J. Am. Chem. Soc.* 105:6442-55, 1983). The peptide can be extracted with 20% acetic acid, lyophilized, and purified by reversed-phase HPLC on a Vydac C-4 Analytical Column using a linear gradient of 100% water to 100% acetonitrile-0.1% trifluoroacetic acid in 50 minutes. The peptide is analyzed using PTC-amino acid analysis (Heinrikson et al., *Anal. Biochem.* 136:65-74, 1984). After gas-phase hydrolysis (Meltzer et al., *Anal. Biochem.* 160: 356-61, 1987), sequences are confirmed using the Edman degradation or fast atom bombardment mass spectroscopy. After synthesis, the polymeric carriers can be tested for drug binding using size-exclusion HPLC, as described above, or any of the other analytical methods listed above.

The polymeric carriers of the present invention preferably comprise more than one drug-binding domain. A polypeptide comprising several drug-binding domains may be synthesized. Alternatively, several of the synthesized drug-binding peptides may be joined together using bifunctional cross-linkers, as described below.

The second synthetic mechanism involves the determination of a DNA sequence which will encode the desired amino acid sequence (i.e., the amino acid sequence of the drug-binding peptide fragment determined above). Such a DNA sequence may be determined because the genetic code (i.e., the three-base sequence or codon in an mRNA which specifies a given amino acid) is known. A DNA sequence which encodes the polymeric carrier may be synthesized in vitro by standard oligonucleotide synthesis procedures. See, for example, U.S. Pat. Nos. 4,500,707 and 4,668,777. The synthetic DNA fragment encoding the polymeric carrier is cloned and expressed using recombinant DNA technology.

When a polymeric carrier containing multiple copies of a drug-binding domain is desired, a DNA sequence that encodes a polypeptide comprising multiple copies of the drug-binding peptide fragment is synthesized. Alternatively, multiple copies of the oligonucleotide encoding the domain may be ligated together by conventional procedures (e.g., using the enzyme T4 DNA ligase). The resulting DNA sequence encodes a polypeptide comprising multiple drug-binding domains. Such polypeptides are useful as polymeric carriers that bind several drug molecules non-covalently. The DNA sequences encoding these polymeric carriers may be cloned and expressed through recombinant DNA technology.

Many suitable methods for inserting a DNA sequence of interest into a microbial host to generate recombinant microorganisms which produce the polypeptide encoded by the DNA are known. Microorganisms which have been used as host cells include, but are not limited to, prokaryotes, such as gram-negative and gram-positive bacteria, and eukaryotes, such as yeast or mammalian cell lines. In general, the DNA sequence is inserted in vitro into a vector capable of replication in certain host microorganisms. The vector typically is derived from a plasmid or a virus.

A number of cloning vector/host cell systems have been developed including vectors suitable for transforming the gram-negative bacterium *E. coli* (Old and Primrose, *Principals of Gene Maniplation*, 2d ed. , Univ. of California Press, 1981, pp. 32–35 and 46–47), gram-positive bacteria *Bacillus subtilis* (Old and Primrose, pp. 51–53), or eukaryotic microorganisms such as yeast (Old and Primrose, pp. 62–68). "Shuttle vectors," which may be transferred (along with the cDNA they carry) between the host microorganisms, *E. coli* and yeast, have been described by Storms et al., *J. Bacteriology* 140:73–82, 1979; and Blanc et al., *Molec. Gen. Genet.* 176:335–42, 1979. Shuttle vectors also exist which replicate in both *E. coli* and *B. subtilis* (Old and Primrose, at p. 53). Vectors derived from bacteriophages such as M13 have also been useful in the cloning of foreign genes (Old and Primrose, Chapter 5).

Known procedures are used for inserting the DNA into a suitable vector, e.g., homopolymeric tailing, blunt-end ligation, or by use of linker molecules (Old and Primrose, at p.92). Microbial host cells are transformed with the resulting recombinant cloning vectors, and the transformants are screened using conventional procedures, which vary according to the particular gene and vector/host system used to identify transformants containing the desired cloned cDNA.

The cloned DNA sequence generally is transferred to an appropriate "expression vector," although certain vectors that have been developed play the dual roles of both cloning and expression vectors. An expression vector comprises "expression signals," i.e., sequences such as promotors and operators, which are required for the transcription of DNA into messenger RNA (mRNA). This is followed by translation of the mRNA into protein (i.e., the polypeptide encoded by the DNA sequence). The expression signals are functional in the intended host cell. The DNA sequence of interest is "operably linked" to the expression signals by insertion of the DNA into the vector in a position downstream from the expression signals such that the first codon of the protein-encoding sequence is in the same reading frame as an initiation codon. Examples of some of the many expression vectors which have been developed for use in recombinant DNA technology include those described by Old and Primrose, pp. 104–17; PCT patent application Publication No. WO 86/00528; U.S. Pat. Nos. 4,599,311 and 4,704,362; and British Patent No. GB 2,119,804.

An appropriate microorganism strain is transformed with the recombinant expression vector, then cultured in a suitable growth medium under conditions appropriate for production of the desired polypeptide. Expression vector systems may be engineered so that expression of the foreign protein may be regulated by chemical or temperature induction. Proteins which are secreted out of the host cells may be isolated from the growth media by conventional protein purification procedures. When the desired protein remains inside the host cells, the cells are harvested and then lysed through procedures which may be mechanical (e.g., sonication, homogenization, freeze-thawing, nitrogen compression-decompression, etc.), chemical (e.g., treatment with detergents such as sodium dodecyl sulfate, guanidine HCl or NP-40), enzymatic (such as by using lysozyme), or combinations thereof. The desired polypeptide is then purified from the lysate using conventional procedures.

The polypeptides produced by cloning and expressing DNA sequences encoding one or more drug-binding domains are used as polymeric carriers. The recombinant cells may be cultured to produce large quantities of the polymeric carrier polypeptides, and these carriers may be attached to various targeting proteins to form conjugates capable of non-covalently binding drug molecules.

When the amino acid sequence of a drug-binding protein is known, drug-binding domains can be isolated without prior enzymatic or chemical digestion of the protein. For example, the sequence of chicken riboflavin-binding protein is known (Protein Information Resource Protein Sequence Data Bank). In order to search for a riboflavin-binding domain, 40-amino-acid-long peptides, overlapping by 20 amino acids, can be synthesized from the known sequence of this 219-residue protein. The peptides are synthesized as described above, using manual procedures or a commercially available synthesizer. Each synthetic peptide can then be tested for drug binding. By comparison of the sequence of the overlapping peptides which bind drugs, those residues important for drug binding can be identified. A peptide comprising the drug-binding domain can then be replicated and conjugated to form a polymeric carrier according to the procedures described below.

When several proteins are known to bind the same or similar drugs, it may be possible to identify the drug-binding domain within each of the proteins by identifying homologous amino acid sequences within the proteins. Alternatively, when the amino acid sequence of the drug-binding domain of one protein that binds a drug of interest is known, a computer search for homologous sequences may be run on a large protein sequence data bank. Additional proteins that may bind the particular drug of interest thus may be found. Through either of these approaches, drug-binding domains may be identified without running drug-binding assays on a large number of peptide fragments representing the entire amino acid sequence of a protein.

Another process for isolating a polymeric carrier involves cloning the gene which encodes a large molecular weight protein that can non-covalently bind to a drug of interest. Procedures for isolating and cloning DNA sequences which encode such proteins are known. See, for example, Lawn et al., *Nucleic Acids Research* 9:6103-14, 1981, in which isolation of cDNA which encodes the human serum albumin (HSA) protein is described.

A cloned gene encoding a drug-binding protein may be isolated from a recombinant microorganism and fragmented using restriction endonucleases. The resulting gene fragments are subcloned and expressed in a suitable host/vector system, thereby producing fragments of the drug-binding protein. The peptide fragments produced by the various recombinant microorganisms transformed with the subcloned DNA are analyzed for drug-binding ability. Recombinant cultures producing peptide fragments comprising the drug-binding domain thus are identified. Cultivation of the recombinant cells produces the peptide fragment for use as a polymeric carrier.

While a single drug-binding domain may be attached to a targeting protein in certain cases, it is often desirable to attach more then one drug molecule to a targeting protein. In such cases, the polymeric carrier preferably comprises more than one drug-binding domain. Conjugates of such polymeric carriers and targeting proteins may be used to deliver multiple drug molecules to target cells, thus enhancing the therapeutic effect against the target cells.

These polymeric carriers comprising more than one drug-binding domain may be derived from the peptides containing single domains which are produced by any of the above-described methods. Several drug-binding domains can be covalently joined together, after refolding, using bifunctional linkers to form polymeric carriers. The linkers are selected to give optimal polymerization and generally consist of variable-length spacer groups with a chemically reactive group at each end. The two chemically reactive groups may be the same or different, and each will react with a functional group on a peptide fragment, thereby joining peptide fragments together through the linker.

Among the many possible chemically reactive groups that a linker may comprise are amine-reactive groups such as esters and sulfhydryl-reactive groups such as maleimides. The spacer portion of the linker preferably is large enough to reduce steric hindrance during reaction with the peptide fragments, yet small enough so that the linker molecules used to form a multi-domain polymeric carrier do not significantly increase the molecular weight of the carrier. The spacer may, for example, comprise a chain of from two to four methylene groups or a single cyclohexane ring.

Many suitable linkers are known, examples of which include dimethylsuberimidate, bis-(sulfosuccinimidyl) suberate, and sulfosuccinimidyl -(4'-azido-2'-nitrophenylamino) hexanoate. Other suitable crosslinkers and the use thereof are described in the Pierce Chemical Company 1988 Handbook and General Catalog, pages 222-243. An isolated domain could be polymerized by introducing two surface thiols on opposite faces of the structure (if it doesn't already have cysteines) and air-oxidizing.

The resulting multiple drug-binding domain polymeric carriers should not be so large as to adversely affect the immunoreactivity or other properties of the targeting protein. Advantageously, the polymeric carrier is less than 60 kilodaltons. When water solubility is an important characteristic of the resulting targeting-protein conjugate, the size of the carrier may have to be further reduced.

The total size of the polymeric carrier will vary according to such factors as the therapeutic activity of the particular drug to be used (e.g., whether attachment of multiple drug molecules to the carrier is desirable), the susceptibility of a particular targeting protein to loss of targeting ability when a high molecular weight polypeptide (i.e., the carrier) is attached thereto, and the size of the drug-binding peptide(s) from which the polymeric carrier is formed. In one embodiment of the invention, a polymeric carrier comprises from two to twenty, preferably from two to about ten, drug-binding domains. The polymeric carrier preferably has a molecular weight of about 35 kilodaltons or less.

The drug-binding domains employed in the present invention are derived from drug-binding proteins. The term "derived from a protein" as used herein is not limited to actual physical isolation from a protein. The process of producing the polymeric carriers of the invention generally begins with identification of a drug-binding domain within a protein. Once the domain is characterized (e.g., by determination of the amino acid sequence), multiple copies of the domain may be produced by synthetic methods that include peptide synthesis and recombinant DNA technology.

In addition, the polymeric carriers may comprise drug-binding domains that are modifications of the domains found in the parent protein. These modifications include, among others, changes in the amino acid sequence (e.g., to achieve tighter drug binding) or incorporation of additional peptides that confer desirable properties such as improved water solubility on the polymeric carrier. Thus, domains "derived from a protein" may be produced by totally synthetic means, rather than being isolated from the parent protein, and may not be identical to the drug-binding domain found in the parent protein. The polymeric carriers are produced using information obtained through identifying and characterizing drug-binding domains within the parent proteins.

The choice of a particular polypeptide for use as a polymeric carrier may be influenced by several factors. Stability of the non-covalent drug binding to the drug-binding domain is one such factor. When a conjugate of the invention is to be included in a water-soluble pharmaceutical composition, the water solubility of the polymeric carrier component of the conjugate is considered. The polymeric carrier may comprise amino acid sequences extraneous to the actual drug-binding domain. Certain amino acid residues may be added at the termini of the domain-containing peptide, wherein the amino acid residues comprise chemically reactive groups that will react with one of the above-described bifunctional cross-linkers. Alternatively, amino acid sequences may be added to the drug-binding domain in order to achieve the secondary structure required for a particular desirable biological property. Various amino acid sequences may be added during peptide synthesis or DNA synthesis to the peptide fragment originally derived from the drug binding protein. These amino acid sequences may be chosen to increase the water solubility of the resulting polymeric carrier, for example. Such sequences may be chosen based on knowledge of the sequences that confer hydrophilicity on other known proteins, for example.

In some cases, it may be desirable to prepare conjugates of the present invention that comprise more than one type of drug. This is especially advantageous when two or more drugs have a synergistic therapeutic effect on the target cells. Administration of more than one type of drug is desirable in the treatment of certain diseases such as cancer, especially in view of the heterogeneous cell populations found within some tumors.

Thus, a polymeric carrier of the present invention may comprise two or more different types of drug-binding domains. The domains are each isolated from different large molecular weight proteins, then are joined to form a polymeric carrier, using the procedures described above. Alternatively, a particular drug-binding domain may be capable of binding more than one type of drug. Polymeric carriers comprising multiple copies of such a domain may be incubated with the different drugs to bind two or more different types of drugs to the polymeric carrier.

Any suitable procedure may be used for non-covalently binding a drug of interest to the polymeric carrier. In general, an excess of the drug is incubated with the carrier in a buffered aqueous solution to bind the drug to the carrier.

A polymeric carrier of the present invention, having one or more drug molecules bound thereto, is administered to a human or mammalian host for therapeutic purposes. These polymeric carriers are useful as slow-release drug delivery systems.

Alternatively, the polymeric carriers produced by the above-described procedures may be attached to targeting proteins. The targeting protein serves to deliver the conjugate to a specific cellular or tissue target site when administered in vivo. The targeting is preferably accomplished by immune selectivity through antigen/antibody interactions.

Suitable targeting proteins include, but are not limited to, antibodies and antibody fragments; serum proteins; enzymes; peptide hormones; and biologic response modifiers. Among the suitable biologic response modifiers which may be used are lymphokines such as interleukins (e.g., IL-1, -2, -3, -4, -5, and -6) or interferons (e.g., alpha, beta, and gamma interferon), erythropoietin, and colony stimulating factors (e.g., G-CSF, GM-CSF, and M-CSF). Peptide hormones include melanocyte stimulating hormone, follicle stimulating hormone, luteinizing hormone, and human growth hormone. Enzymes include fibrinolytic enzymes such as tissue-type plasminogen activator, streptokinase, and urokinase. Serum proteins include human serum albumin.

These proteins may be modified; e.g., to produce variants and fragments of the proteins, as long as the desired biological property (i.e., the ability to bind to the target site) is retained. The proteins may be modified by using various genetic engineering or protein engineering techniques. Another type of modification involves chemically modifying targeting proteins to effect a shift in the isoelectric point of the resulting "charge modified" protein, as described in co-pending U.S. patent application Ser. No. 157,273, entitled "Alteration of Pharmacokinetics of Proteins by Charge Modification" filed Feb. 17, 1988. The serum half-life, biodistribution, immunogenicity, and other properties of targeting proteins may be altered by modifying the charge of the protein.

The antibodies employed as targeting proteins in the present invention may be intact antibody molecules, fragments thereof, or functional equivalents thereof, including genetically engineered variations thereof. Examples of antibody fragments are F(ab')$_2$, Fab', Fab, and Fv fragments, which may be produced by conventional procedures or by genetic or protein engineering. While polyclonal antibodies may be employed in the present invention, monoclonal antibodies (MAbs) are preferred. A number of monoclonal antibodies that bind to a specific type of cell have been developed, including MAbs specific for tumor-associated antigens in humans. Among the many such MAbs that may be used are anti-TAC or other interleukin-2 receptor antibodies, 9.2.27 and NR-ML-05 to the 250-kilodalton human melanoma-associated proteoglycan; NR-LU-10 to the 37 to 40-kilodalton pancarcinoma glycoprotein; and OVB3 to an as yet unidentified tumor-associated antigen.

A variety of procedures may be used to attach the polymeric carrier to a targeting protein, such as an antibody. Both the polymeric carrier and the targeting protein are polypeptides which contain a variety of functional groups, e.g., carboxylic acid (COOH) or free amine (—NH$_2$) groups, which are available for reaction with a suitable functional group to covalently bind the polymeric carrier to the targeting protein. For example, reaction with a water-soluble carbodiimide coupling reagent may be used to form bonds between a free amino group on one reactant species and a COOH group on the other reactant species.

Alternatively, the antibody and/or polymeric carrier may be derivatized to expose or attach additional reactive functional groups. The derivatization may involve attachment of any of a number of linker molecules, such as those available from Pierce Chemical Company, Rockford, Ill. (see Pierce 1988 General Catalog, pp. 221–250). Alternatively, derivatization may involve chemical treatment of the antibody, e.g., oxidative cleavage of vicinal hydroxyls on the sugar moiety of a glycoprotein antibody with periodate to generate free aldehyde groups. The free aldehyde groups on the antibody may be reacted with free amine groups on the polymeric carrier to form the desired bond. See U.S. Pat. No. 4,671,958. Procedures for generation of free sulfhydryl groups on antibodies or antibody fragments are also known. See U.S. Pat.No. 4,659,839. Many procedures and linker molecules for attachment of various compounds to proteins such as antibodies are known. See, for example, U.S. Pat. Nos. 4,671,958; 4,414,148; 4,046,722; 4,699,784; and 4,680,338.

A polymeric carrier/drug conjugate or a targeting protein/polymeric carrier/drug conjugate of the present invention may be administered for therapeutic purposes to a human or mammalian host by any suitable means. The conjugate may be administered intravenously, intraarterially, or peritoneally, for example, with the choice being determined by such factors as the location of the target site(s) within the body. The dosage will vary according to such factors as the type of drug in the conjugate, the number of drug molecules attached to the polymeric carrier, and the specificity of the targeting protein. A physician skilled in the field to which this invention pertains will be able to determine the proper dosage of a given conjugate.

The conjugates of the present invention may be administered in the form of a suitable pharmaceutical composition. In one embodiment of the invention, a pharmaceutical composition comprises an aqueous solution containing a targeting protein/polymeric carrier/drug conjugate or other conjugate of the invention. In an alternative embodiment, the pharmaceutical composition is in solid (e.g., freeze-dried) form, to be dissolved in an aqueous solution prior to injection into the patient. The pharmaceutical preparation may additionally contain conventional stabilizers, excipients, and the like. The preparation is injected into a patient for therapeutic purposes.

The following examples illustrate the use of the process of this invention to form novel polymeric carriers to non-covalently bind drugs. Procedures for preparing conjugates comprising a drug non-covalently bound to a polymeric carrier that is attached to a targeting protein such as an antibody also are described. These examples are offered by way of illustration of the invention and not by way of limitation.

EXAMPLE 1

Synthesis of an Adriamycin-Binding Polymeric Carrier

In this example, the drug adriamycin (i.e., doxorubicin) is bound to polymeric carriers derived from chicken riboflavin-binding protein (CRBP). Riboflavin-binding protein is used as the source of the polymeric carrier because this compound is known to non-covalently bind adriamycin. Other anthracycline drugs may be used in place of or in addition to adriamycin in the following procedures. The sequence of CRBP is known (Protein Information Resource Data Bank, release 14 (1987)). The sequence of CRBP contains 5 arginines and 7 methionines. Thus, the proteolytic enzyme arg-C-endoprotease and the chemical peptide digestion agent cyanogen bromide are used initially to generate fragments for testing of drug (adriamycin) binding. Other chemical cleavage methods or proteases could also be used. For cleavage of the peptide at Arg residues, the fragments are 56, 20, 7, 5, 37 and 92 amino acid residues long. For methionine cleavage, the amino acid fragments are 21, 122, 7, 4, 17, 5, 17 and 25 residues long.

The CRBP protein cystines are reduced for one day at 37° C. in 6M guanidine hydrochloride at pH 8.5 in 0.1M tris buffer with a 100-fold excess of dithiothreitol (DTT) to protein cysteines The cysteines may be carboxymethylated with a 5-fold excess of iodoacetic acid to DTT thiols for one hour at 37° C. The protein is microdialyzed against water, or an appropriate buffer for digestion. For cyanogen bromide digestion, 200 μg protein is dissolved in 400 μl of 70% formic acid containing 100 moles of cyanogen bromide per mole methionine, and reacted in the dark, under nitrogen for 24 hours at 37° C. After digestion, the mixture is diluted 10-fold with water, lyophilized, run over a Vydac C-4 5μ 0.4×25 cm reversed-phase column. Elution is with a gradient of 1% per minute from water plus 0.1% trifluoroacetic acid (TFA) to 100% acetonitrile plus 0.1% TFA.

Alternatively, 200 μg reduced (or reduced and carboxymethylated) CRBP protein is dissolved in 0.1M sodium bicarbonate, pH 8.0, and digested with 10 μg submaxillaris protease (an arg-C-endoprotease) for 14 hours. The fragments are purified as above.

The purified protein fragments (obtained by either chemical or enzymatic digestion) are incubated in 0.1M phosphate or 0.1M hepes buffer at pH 7.0 for 1 hour with a 100-fold excess of adriamycin and then eluted over an appropriate gel-filtration column. The peptide peak is checked spectro-photometrically for elution peaks at 280 nm and 495 nm to detect bound adriamycin. This procedure can be repeated with other peptide fragments or other digestion product fragments until a tight binding fragment (preferably Kd approximately less than or equal to 1 uM, as measured by equilibrium dialysis or a fluorescence or spectrophotometric titration) is discovered.

Smaller versions (i.e., subfragments) of the peptide fragment may be synthesized by solid-phase synthesis methodology, as mentioned above, to find the minimal size binding domain, which will tightly bind to the drug adriamycin.

Alternatively, peptides about 30–50 amino acid residues in length, overlapping by 15 residues, can be synthesized using the solid-phase peptide synthesis methodology (described above) from the known CRBP sequence. These peptides can be tested for adriamycin binding as above.

The polymerization of the minimal length peptides retaining tight binding to adriamycin is achieved using bifunctional cross-linking reagents. The choice of cross-linking reagent depends on the amino acid composition of the adriamycin-binding domain. If the adriamycin-binding domain contains 2 or more lysine residues, for example, polymerization may be achieved using amine-reactive, bifunctional cross-linking reagents, such as bis(sulfosuccimidyl) suberate. Polymerization is achieved after binding of the drug binding domain to adriamycin. A 100-fold excess of the drug is incubated with the peptide in a buffered solution, as described above. A 0.1M solution of peptide/adriamycin, isolated by size-exclusion chromatography, then is mixed with an equimolar solution of bis(sulfosuccimidyl) suberate at pH 8.0-9.0 in 0.05M hepes buffer. Aliquots are withdrawn periodically for analysis. The aliquots are run on a 20% SDS gel or over a size-exclusion column to monitor the extent of polymerization. A distribution of polymer length results when the conditions are optimized for a particular length polymer. Advantageously, the polymeric carrier comprises less than 20 copies of the drug-binding domain. The resulting polymerized polymeric carrier having adriamycin bound thereto can be purified as necessary by size-exclusion HPLC.

The polymeric carrier bound to adriamycin is attached to the targeting protein by a similar cross-linking procedure. The procedure may vary according to the type of targeting protein used. One of the methods described above for attaching carriers to targeting proteins to form conjugates of the invention (e.g., through the use of bifunctional cross-linkers) may be used.

EXAMPLE 2

Isolating a DNA Sequence Which Encodes a Polymeric Carrier

A gene encoding human serum albumin is cloned in a plasmid vector using the procedures of Lawn et al. (*Nucleic Acids Research*, 9:6103-14, 1981). Human serum albumin (HSA)-specific DNA is isolated by digesting the recombinant vector with the restriction enzyme Pst I. Samples of the HSA-specific cDNA are subjected to further digestion with several different restriction enzymes in separate reaction mixtures. The resulting DNA fragments are separated by electrophoresis on agarose gels, purified from the gel, and subcloned into plasmid expression vectors comprising regulatory signals functional in *E. coli* cells, such as the trp promoter-operator. *E. coli* HB101 cells are transformed with the resulting plasmids and cultured to produce the HSA protein fragments encoded by the HSA gene fragments. These protein fragments are purified from samples of each culture by a standard procedure, such as immunoprecipitation, followed by SDS polyacrylamide gel electrophoresis. See Kessler, *J. Immunology* 117:1432-90, 1976; and Laemmli, *Nature* 277:680-85, 1970.

Each protein fragment is analyzed to determine its ability to bind a drug of interest by one of the procedures described above. For example, the drug adriamycin is combined with each protein fragment and the samples are each analyzed to detect free versus protein-bound drug. One method of analysis involves subjecting the protein fragment samples (either purified or in the form of the *E. coli* cell lysates) to electrophoresis on an SDS-polyacrylamide gel. The fragments (separated according to molecular weight) are transferred from the gel to a nitrocellulose sheet in accordance with the known "Western blot" technique. A solution containing adriamycin is contacted with the nitrocellulose sheet. After washing the nitrocellulose sheet to remove non-bound drug, the polypeptide bands which bind the drug will appear red, the color imparted by adriamycin. The culture(s) found to produce a relatively small protein fragment with sufficient affinity for the drug are cultured to produce the polymeric carrier (i.e., the HSA protein fragment) on a larger scale. Alternatively, the amino acid sequence of the peptide fragment may be determined, and the fragment may be produced by peptide synthesis procedures.

When a polymeric carrier comprising multiple drug-binding domains is desired, multiple copies of the peptide fragment produced above may be joined together using a bifunctional cross-linker. A number of different cross-linkers may be used, depending on the amino acid sequence of the peptides to be joined. The linker may be chosen from those described in the Pierce Chemical Company Catalog, as discussed above. One cross-linking procedure is presented in Example 1.

An alternative method for producing the polymeric carrier involves determining the amino acid sequence of the peptide fragment, synthesizing a DNA sequence that encodes a polypeptide comprising at least one copy of the peptide fragment, expressing the DNA sequence in recombinant host cells (thereby producing the polypeptide), and purifying the polypeptide from the recombinant cells for use as a polymeric carrier. The DNA sequence may encode a polymeric carrier comprising multiple drug-binding domains. Alternatively, multiple copies of a single drug-binding peptide fragment produced by the recombinant cells may be purified and enzymatically ligated together to form multi-domain polymeric carriers.

EXAMPLE 3

Preparation of a Polymeric-Carrier-Antibody Conjugate

A polymeric carrier such as one produced as described in Example 1 or 2 is covalently bound to an antibody as follows. This is an alternative procedure to the methods for forming conjugates described in Example 1.

The polymeric carrier is conjugated to a monoclonal antibody through a thioether linkage. The polymeric carrier is first reacted with succinimidyl 4-(N-maleimido-methyl)cyclohexane-1-carboxylate (SMCC) at a molar ratio of 1:10 (carrier:linker). Excess heterobifunctional linker reagent is removed from derivatized polymeric carrier by gel filtration. The antibody is treated with 25 mM dithio-threitol (DTT) in 0.01M phosphate-buffered saline (PBS), pH 7.5, and excess DTT is removed by gel filtration. The derivatized polymeric carrier and the reduced antibody components are mixed and incubated at room temperature for 15+ minutes.

The conjugation reaction mixtures are then fractionated by FPLC gel filtration on a TSK 3000 column at 0.5 ml/min to separate the immunoconjugate from unconjugated antibody and unreacted derivatized carrier.

If a drug were not bound to the polymeric carrier prior to the step of conjugation to the antibody, the resulting immunoconjugate is mixed with the drug in a buffered solution, whereby the drug becomes associated with the polymeric carrier. Non-bound drug is removed by gel filtration or dialysis. The thus-produced conjugate of the present invention may be administered to a patient bearing a target site to which the antibody binds, wherein the target site is to be treated with the drug. The antibody may be a monoclonal antibody that binds to a tumor, and the drug is an anti-cancer drug.

EXAMPLE 4

Polymeric Carriers Isolated from HSA

The full-length protein human serum albumin (HSA) is purified from human blood plasma or from recombinant cells by known procedures. See, for example, U.S. Pat. Nos. 4,684,723; and Lawn et al., *Nucleic Acids Research*, Vol. 9, No 22, 1981. The protein is subjected to digestion with a proteolytic enzyme to generate polypeptide fragments which are separated by electrophoresis (e.g., on an SDS-polyacrylamide gel). The ability of each polypeptide fragment to bind a particular drug of interest is analyzed by procedures which detect protein-bound drug versus free drug, such as those described in Examples 1 and 2. The drug is a drug that the parent protein binds non-covalently (see Table I).

Drug-binding polypeptide fragments suitable for use as polymeric carriers thus are identified. If desired, smaller peptide fragments may be generated by enzymatic or chemical cleavage of the thus-identified drug-binding polypeptide fragment. The drug-binding assay is repeated on the smaller fragments to identify the smallest peptide fragment comprising a drug-binding domain. The amino acid sequence of each carrier is determined using the standard Edman degradation process, as described above. Once the amino acid sequence is determined, the carriers are synthesized as needed using a commercially available peptide synthesizer. Multi-domain polymeric carriers may be produced by joining multiple copies of the peptide together using bifunctional linkers.

Alternatively, a DNA sequence which encodes the desired amino acid sequence (preferably multiple copies thereof) is synthesized in vitro. The synthesized DNA sequence is inserted into an appropriate expression vector and appropriate host cells are transformed with the recombinant vector. The cells are subjected to an appropriate screening process to identify recombinant cells producing the carrier polypeptide of interest. For example, lysates of samples of the cultures may be subjected to gel electrophoresis to identify those producing a polypeptide of the size expected for the carrier polypeptide. Further analysis may involve one of the above-described drug-binding assays.

A recombinant microbial strain producing the desired carrier polypeptide is cultured on a larger scale to produce the carrier polypeptide as needed.

EXAMPLE 5

Pharmaceutical Composition Comprising Polymeric Carrier and Drug

A single- or multi-domain version of the polymeric carrier derived from RBP is reacted with doxorubicin and/or other anthracyclines as described in Example 1. Unbound drug is removed by gel filtration. Carrier-bound drug is then lyophilized with a typical additive such as lactose. Upon reconstitution to form an aqueous solution, the composition is administered to patients with tumors. Improved tumor delivery and less cardiac toxicity (compared to administration of the free drug) are expected to be achieved, thereby allowing higher dose levels as well as administration to patients who are no longer eligible for treatment with adriamycin because of cumulative cardiac toxicity. The slow release of the drug from the polymeric carrier also maintains higher serum concentrations for longer periods of time.

From the foregoing, it will be appreciated that, although specific embodiments of the invention have been described herein for purposes of illustration, various modifications may be made to the invention without departing from the spirit and scope of the invention.

We claim:

1. A targeting protein/polymeric carrier/drug conjugate comprising a targeting protein covalently bound to a polymeric carrier that comprises a drug-binding domain derived from a drug-binding protein, and a drug non-covalently bound to the polymeric carrier, wherein the polymeric carrier does not comprise an entire drug-binding protein, but is derived from a drug-binding domain of said drug-binding protein, wherein the molecular weight of the polymeric carrier is less than about 60,000 daltons, and wherein said drug is an anti-cancer anthracycline antibiotic, cis-platinum, methotrexate, vinblastine, mitoxantrone, ARA-C, 6-mercaptopurine, 6-mercaptoguanosine, mitomycin C or a steroid.

2. A targeting protein/polymeric carrier/drug conjugate comprising a targeting protein covalently bound to a polymeric carrier, and a drug non-covalently bound to the polymeric carrier, wherein the polymeric carrier comprises from 2 to about 20 drug-binding domains derived from drug-binding protein;
   wherein the polymeric carrier does not comprise an entire drug-binding protein, but is derived from drug-binding domains of said drug-binding protein(s), and the molecular weight of the polymeric carrier is less than about 60,000 daltons.

3. The conjugate of claim 1 or 2 wherein the drug is selected from the group consisting of an anti-cancer anthracycline antibiotic, cis-platinum, and methotrexate, and the drug-binding protein is an albumin.

4. The conjugate of claim 1 or 2 wherein the drug is a steroid and the drug-binding protein is a steroid-binding protein.

5. The conjugate of claim 4 wherein the drug is an estrogen or derivative thereof and the drug-binding protein is an estrogen receptor.

6. The conjugate of claim 1 or 2 wherein the drug is selected from the group consisting of an anti-cancer anthracycline antibiotic, vinblastine, mitoxantrone, ARA-C, 6-mercaptopurine, 6-mercaptoguanosine, and mitomycin C, and the drug binding protein is $\alpha$-1-acid glycoprotein.

7. The conjugate of claim 1 or 2 wherein the drug is an anti-cancer anthracycline antibiotic, and the drug-binding protein is riboflavin-binding protein.

8. The conjugate of claim 2 wherein the polymeric carrier comprises from 2 to about 10 drug-binding domains.

9. The conjugate of claim 2 wherein the drug-binding domains are joined through bifunctional cross-linkers.

10. The conjugate of claim 2 wherein the polymeric carrier has from 2 to about 20 anti-cancer drugs bound thereto.

11. The conjugate of claim 1 or 2 wherein the polymeric carrier comprises a peptide that increases the water solubility of the polymeric carrier.

12. The conjugate of claim 1 or 2 wherein said targeting protein is selected from the group consisting of antibodies, serum proteins, hormones, enzymes, biologic response modifiers, and fragments thereof.

13. The conjugate of claim 12 wherein said targeting protein is a monoclonal antibody or a fragment thereof.

14. The conjugate of claim 13 wherein said monoclonal antibody or fragment thereof binds to cancer cells.

15. A slow-release pharmaceutical composition having therapeutic use comprising a conjugate of claim 1 in an aqueous solution.

16. The conjugate of claim 3 wherein the anti-cancer anthracycline antibiotic is doxorubicin or daunorubicin.

17. The conjugate of claim 6 wherein the anti-cancer anthracycline antibiotic is doxorubicin or daunorubicin.

18. The conjugate of claim 7 wherein the anti-cancer anthracycline antibiotic is doxorubicin or daunorubicin.

* * * * *